United States Patent
Smith (10) Patent No.: US 9,802,002 B2
(45) Date of Patent: Oct. 31, 2017

(54) TRAINING CARTRIDGE FOR A DRUG DELIVERY DEVICE

(75) Inventor: Christopher James Smith, Cheshire (GB)

(73) Assignee: Sanofi-Aventis Deutschland GmbH, Frankfurt am Main (DE)

(*) Notice: Subject to any disclaimer, the term of this patent is extended or adjusted under 35 U.S.C. 154(b) by 1083 days.

(21) Appl. No.: 13/699,316

(22) PCT Filed: May 31, 2011

(86) PCT No.: PCT/EP2011/058925
§ 371 (c)(1),
(2), (4) Date: Mar. 18, 2013

(87) PCT Pub. No.: WO2011/151315
PCT Pub. Date: Dec. 8, 2011

(65) Prior Publication Data
US 2013/0172824 A1   Jul. 4, 2013

(30) Foreign Application Priority Data
Jun. 2, 2010  (EP) .................................... 10164701

(51) Int. Cl.
*A61M 5/315*   (2006.01)
*A61M 5/178*   (2006.01)
(Continued)

(52) U.S. Cl.
CPC ........ *A61M 5/31573* (2013.01); *A61M 5/178* (2013.01); *G09B 19/003* (2013.01); *G09B 19/24* (2013.01); *G09B 23/285* (2013.01)

(58) Field of Classification Search
CPC ........ A61M 5/3134; A61M 2005/3123; A61M 2005/3132; G09B 19/003; G09B 19/24; G09B 23/285
See application file for complete search history.

(56) References Cited

U.S. PATENT DOCUMENTS

| 533,575 A | 2/1895 | Wilkens |
| 3,318,021 A | 5/1967 | Sarnoff |

(Continued)

FOREIGN PATENT DOCUMENTS

| EP | 0937471 A2 | 8/1999 |
| EP | 0937476 A2 | 8/1999 |

(Continued)

OTHER PUBLICATIONS

Form PCT/IB/326, Notification Concerning Transmittal of International Preliminary Report on Patentability.
(Continued)

*Primary Examiner* — Matthew F DeSanto
(74) *Attorney, Agent, or Firm* — McDonnell, Boehnen, Hulbert & Berghoff LLP (57) ABSTRACT

The present invention provides test or training a cartridge for a drug delivery device as well as a method for resetting of such cartridge, wherein the cartridge comprises: a body of substantially cylindrical shape, a piston slidably disposed in the body in an axial direction, a closure means disposed at an axial end portion of the body, wherein the body, the piston and the closure means confine an interior volume coupled to the exterior via at least one fluid escape channel.

11 Claims, 6 Drawing Sheets

(51) Int. Cl.
  *G09B 19/00* (2006.01)
  *G09B 19/24* (2006.01)
  *G09B 23/28* (2006.01)

(56) References Cited

U.S. PATENT DOCUMENTS

| | | | |
|---|---|---|---|
| 3,426,448 A | | 2/1969 | Sarnoff |
| 4,235,235 A | * | 11/1980 | Bekkering .......... A61M 5/3129 |
| | | | 604/238 |
| 4,474,559 A | | 10/1984 | Steiger |
| 5,226,895 A | | 7/1993 | Harris |
| 5,279,586 A | | 1/1994 | Balkwill |
| 5,304,152 A | | 4/1994 | Sams |
| 5,320,603 A | * | 6/1994 | Vetter .................. A61M 5/284 |
| | | | 604/416 |
| 5,320,609 A | | 6/1994 | Haber et al. |
| 5,334,162 A | * | 8/1994 | Harris .................... A61J 1/062 |
| | | | 604/232 |
| 5,383,865 A | | 1/1995 | Michel |
| 5,480,387 A | | 1/1996 | Gabriel et al. |
| 5,505,704 A | | 4/1996 | Pawelka et al. |
| 5,582,598 A | | 12/1996 | Chanoch |
| 5,626,566 A | | 5/1997 | Petersen et al. |
| 5,674,204 A | | 10/1997 | Chanoch |
| 5,688,251 A | | 11/1997 | Chanoch |
| 5,743,886 A | | 4/1998 | Lynn et al. |
| 5,830,193 A | * | 11/1998 | Higashikawa ........ A61M 5/284 |
| | | | 604/191 |
| 5,921,966 A | | 7/1999 | Bendek et al. |
| 5,961,495 A | | 10/1999 | Walters et al. |
| 6,004,297 A | | 12/1999 | Steenfeldt-Jensen et al. |
| 6,033,385 A | * | 3/2000 | Liu ...................... A61M 5/322 |
| | | | 604/110 |
| 6,193,698 B1 | | 2/2001 | Kirchhofer et al. |
| 6,221,046 B1 | | 4/2001 | Burroughs et al. |
| 6,235,004 B1 | | 5/2001 | Steenfeldt-Jensen et al. |
| 6,248,095 B1 | | 6/2001 | Giambattista et al. |
| 6,899,698 B2 | | 5/2005 | Sams |
| 6,936,032 B1 | | 8/2005 | Bush, Jr. et al. |
| 7,241,278 B2 | | 7/2007 | Moller |
| 2002/0052578 A1 | | 5/2002 | Moller |
| 2002/0120235 A1 | | 8/2002 | Enggaard |
| 2003/0050609 A1 | | 3/2003 | Sams |
| 2003/0106824 A1 | * | 6/2003 | Wilmot .................. A61J 1/062 |
| | | | 206/439 |
| 2004/0059299 A1 | | 3/2004 | Moller |
| 2004/0210199 A1 | | 10/2004 | Atterbury et al. |
| 2004/0267207 A1 | | 12/2004 | Veasey et al. |
| 2005/0113765 A1 | | 5/2005 | Veasey et al. |
| 2006/0153693 A1 | | 7/2006 | Fiechter et al. |
| 2007/0111175 A1 | | 5/2007 | Raven et al. |
| 2009/0275916 A1 | | 11/2009 | Harms et al. |

FOREIGN PATENT DOCUMENTS

| | | |
|---|---|---|
| EP | 2039384 | 3/2009 |
| EP | 2042210 A2 | 4/2009 |
| EP | 2180459 | 4/2010 |
| EP | 2221078 A1 | 8/2010 |
| WO | 9938554 A1 | 8/1999 |
| WO | 0110484 A1 | 2/2001 |

OTHER PUBLICATIONS

European Search Report for European App. No. 10164701, dated Dec. 17, 2010.
International Search Report for Int. App. No. PCT/EP2011/058925, dated Aug. 16, 2011.

* cited by examiner

TRAINING CARTRIDGE FOR A DRUG DELIVERY DEVICE

CROSS REFERENCE TO RELATED APPLICATIONS

The present application is a U.S. National Phase application pursuant to 35 U.S.C. §371 of International Application No. PCT/EP2011/058925 filed May 31, 2011, which claims priority to European Patent Application No. 10164701.4 filed Jun. 2, 2010. The entire disclosure contents of these applications are herewith incorporated by reference into the present application.

FIELD OF THE INVENTION

The present invention relates to a cartridge for a drug delivery device and in particular to a training or test cartridge that allows a user to get trained and to become accustomed to the handling of a drug delivery device without the necessity of administering a dose of a medicinal product or placebo, e.g. by injection.

BACKGROUND

Drug delivery devices allowing for multiple dosing of a required dosage of a liquid medicinal product, such as liquid drugs, and further providing administration of the liquid to a patient, are as such well-known in the art. Generally, such devices have substantially the same purpose as that of an ordinary syringe.

Pen-type injectors of this kind have to meet a number of user specific requirements. For instance in case of those with diabetes, many users will be physically infirm and may also have impaired vision. Therefore, these devices need to be robust in construction, yet easy to use, both in terms of the manipulation of the parts and understanding by a user of its operation. Further, the dose setting must be easy and unambiguous and where the device is to be disposable rather than reusable, the device should be inexpensive to manufacture and easy to dispose. In order to meet these requirements, the number of parts and steps required to assemble the device and an overall number of material types the device is made from have to be kept to a minimum.

There exist various training cartridges or syringes to be operably coupled with a drive mechanism of a drug delivery device. When appropriately coupled with the drive mechanism, known training cartridges should provide a realistic feedback to the user on how the drug delivery device and its mechanical components behave during dose setting and dose dispensing procedures. In a simple approach, training cartridges are filled with water or a placebo featuring comparable mechanical properties to the genuine medicinal product originally contained in the cartridge of the same or similar type. Even though such water- or placebo-filled cartridges may provide realistic mechanical feedback of the cartridge itself and for the drug device's drive mechanism and also mimic the visible behaviour of the cartridge, such dummy cartridges might be accidentally confused with genuine cartridges filled with a medicinal product. Consequently, the patient may inject water or placebo instead of the prescribed drug and may thus be treated with an incorrect amount of medicinal product.

Furthermore, when making use of water- or placebo-filled cartridges, any of such training or dummy cartridges must be sterile filled or terminally sterilized in case the contents are injected. This also means that the training or dummy cartridge can only be injected by a single user in order to prevent any potential contamination of the cartridge, e.g. in case the cartridge would be used by several users. Moreover, such water- or placebo-filled cartridges have to be used up within a given shelf life or within their given in-use life.

Alternatively, the water- or placebo-filled cartridges may be used for training purposes without injection of the cartridge contents, for example the user dispenses the cartridge contents into an injection pad or into a container. Although this approach has certain advantages, it does not allow the user to practice the step of needle insertion into the skin. A user may suffer from needle phobia or needle anxiety and find that he is unable to insert the needle into the skin. Furthermore, a user who can insert the needle, but who has limited dexterity or strength, may find that he is unable to dispense the device with the needle inserted, for example due to the particular position that the device must be held in during the injection or due to additional pain caused by an unsteady hand moving the needle during the injection. If needle insertion and completing the dispensing action whilst the needle is inserted form a part of the device training process then the healthcare professional can make a proper assessment of the users' capability and take appropriate action.

With these water- or placebo-filled cartridges it is further disadvantageous, that after discharging, the entire cartridge has to be replaced by a new water- or placebo-filled cartridge. Such single-use disposable liquid-filled training cartridges therefore require a corresponding supply and waste management comparable cartridges filled with a liquid drug.

Other approaches suggest to train the device handling without a cartridge assembled therein. However, this is considered to be generally inadequate for the purpose of providing reasonable visual or tactile feedback to the user. First of all, the user does not receive any mechanical and/or otherwise perceptible feedback typically originating from the cartridge. The injection force as well as the length of injection cannot be appropriately simulated. Also, this method lacks a visual feedback on the axial movement of the cartridge's piston. Additionally, a cartridge substitution or cartridge replacement cannot be simulated. Furthermore, needle attachment and the puncturing of the cartridge's septum by means of an injection needle is not trainable in the absence of a cartridge.

It is therefore an object of the present invention to provide a training or test cartridge for a drug delivery device that simulates the overall behavior of a genuine cartridge to a large extent. Preferably, the training cartridge does not require filling with water or a placebo. It is a further aim of the invention, to provide a training cartridge to be usable by numerous users and which is restorable to its initial configuration. Moreover, the invention focuses on a method of resetting a training cartridge for a drug delivery device and further aims to provide a drug delivery device equipped with such a training cartridge.

SUMMARY

In a first aspect, the invention provides a cartridge for a drug delivery device, which is particularly designed as a training or test cartridge for drug delivery devices such as pen-type injectors. The training or test cartridge according to the present invention is adapted to simulate the mechanical and visual feedback of a genuine liquid drug-filled cartridge when inserted in a drug delivery device and being operably engaged with its drive mechanism.

The training cartridge according to the present invention comprises a body of substantially cylindrical shape and a piston, which is slidably disposed in said body along an axial direction. The piston is slidably arranged in said body along the body's long axis defining the axial direction. The cartridge further comprises a closure means disposed at an axial end portion of the body. The closure means is typically of plug-like shape and serves to at least partially seal the interior of the body. Additionally, body, piston and closure means confine an interior volume, which is coupled to the exterior via at least one fluid escape channel.

In a typical configuration, the plug-like closure means and the piston act as sealing surfaces arranged at opposite axial end portions of the substantially cylindrical body. By means of the at least one fluid escape channel, the piston or bung can be displaced with respect to the body, e.g. under the effect of a driving motion of a drive sleeve or piston rod. In this context, a fluid may constitute a liquid or a gaseous medium. Hence, the fluid escape channel forms a passage for a liquid or a gas contained in the interior volume confined by the body, the piston and the closure means.

In contrast to genuine, liquid drug-filled cartridges, the closure means divides the interior volume from an injection means, e.g. an injection needle or a cannula which is typically coupled with the cartridge. In this way, an injection of gaseous or liquid media contained in the interior volume of the cartridge can be effectively precluded. The body and the closure means of the cartridge substantially form a cupped receptacle for the piston slidably disposed therein. By way of the at least one fluid escape channel, the piston can be displaced towards the closure means without substantially increasing the pressure of the gaseous or liquid fluid contained in the interior volume.

In an alternative embodiment the at least one fluid escape channel may be sized appropriately to offer a recognizable resistance to the escape of the gaseous or liquid fluid contained in the interior volume. The absolute size of the fluid escape channel depends on many parameters such as friction coefficient between piston or bung against glass. In this way, the pressure of the gaseous or liquid fluid contained in the interior volume will increase whilst the piston or bung is being displaced with respect to the body, e.g. under the effect of a driving motion of a drive sleeve or piston rod, and will offer increased resistance to the movement of the piston or bung. Once the driving force is removed the pressure will return to its initial value as the gaseous or liquid fluid contained in the interior volume eventually escapes through the at least one fluid escape channel. Thus the fluid escaping through the at least one fluid escape channel will act as a damper on the piston or bung movement and thus simulate the effect of fluid pressure in a genuine cartridge on the device drive sleeve or piston rod when delivering a genuine medicament.

According to a preferred embodiment of the invention, the fluid escape channel is non-sealable. It is of permanent type and persists during the entire lifetime of the training cartridge, irrespective on whether the cartridge is connected with an injection needle or not.

In another preferred embodiment, the fluid escape channel is disposed at an interface section of body and closure means. Typically, the fluid escape channel at least partially extends in radial direction. This way, the fluid escape channel may open out into the peripheral surface of the housing and/or of the closure means.

In a further preferred embodiment, the at least one fluid escape channel is designed as a groove extending in a contact surface of the interface section of body and/or closure means. Hence, any of the mutually corresponding contact surfaces of body and/or closure means may comprise an at least partially radially extending groove that serves as fluid escape channel. Depending on the geometry of body and closure means, in the respective interface section, said fluid escape channel-forming groove may at least partially extend in radial direction, in axial direction or along any other suitable direction there between.

In a further aspect, the closure means comprises an inward facing fluid-impenetrable end wall and an outward facing socket portion. The socket portion comprises a radially extending shoulder and a stepped down neck portion, wherein the shoulder is adapted to but against a corresponding radially inwardly extending rim of a cartridge holder of the drug delivery device. By having a fluid-impenetrable inward facing end wall, the interior volume of the training cartridge can be effectively divided and separated from an outlet port of the cartridge, which typically is to be connected with an injection means in a fluid-transferring way.

In a further preferred embodiment, the socket portion of the closure means comprises a septum sealing a cupped receptacle, which is separated from the interior volume of the cartridge body, preferably by means of the closure means' end wall. Such septum is commonly designed as rubber stopper providing an air-tight seal but being pierceable by piercing elements such as needles or cannulae. The cupped receptacle sealed by the septum is adapted to receive at least a proximally directed end portion of a piercing element. Since the cupped receptacle is separated and hermetically divided from the cartridge's interior volume, neither gaseous nor liquid media can be transferred from said receptacle to the piercing element. This way, the risk of cross-contamination can be reduced in the event that the training cartridge is to be used by multiple users.

In another embodiment, the socket portion of the closure means comprises a cupped receptacle, which is separated from the interior volume of the cartridge body, preferably by means of the closure means' end wall, and which is not sealed by a septum. The cupped receptacle is adapted to receive at least a proximally directed end portion of a needle or cannula. The design of the drug delivery device and the fluid escape channel of the training cartridge will ensure that any gaseous or liquid media that is expelled from the cartridge's interior volume escapes preferentially from the cartridge holder by a means other than through the attached needle or cannula.

In another preferred embodiment, the closure means is integrally formed with the body. In this way, the body and the closure means form a cupped receptacle, which is adapted to slidingly receive the piston. Preferably, closure means and/or body are at least partially transparent in order to allow a user to visually follow the movement of the piston inside the body during training of dose setting and/or dose dispensing. Preferably, the closure means and/or body may be manufactured from a colour tinted material so that the training cartridge can be visibly differentiated from genuine medicament-filled or placebo-filled cartridges.

According to another preferred embodiment of the invention, the closure means is releasably connectable with both axial end sections of the body. Here, the body preferably comprises a symmetrical shape. In particular, the body comprises identical geometric contours and identical contact surfaces at its opposite axial end portions. In this way, the closure means can be selectively attached and connected to either axial end portion of the body.

Advantageously, the training cartridge provides a resetting or restoring feature, which is beneficial in the event when the piston has reached a last stop position. Then, the closure means can be detached from the body, the body itself can be turned about by 180° and the closure means can be re-assembled to the diametrically opposite end of the body. Hence, the reset or restored training cartridge can be re-used and can be reinstalled inside the cartridge holder of the drug delivery device.

In other embodiments, wherein the closure means and the body are integrally formed as a single piece, instead of detaching closure means and body it is conceivable, to retract the piston, e.g. by means of the piston rod, which for this purpose is mechanically engaged with the piston, e.g. in a bi-directional force-transferring way.

According to another preferred embodiment of the invention, the body at its axial end portion comprises a stepped down rim portion, that radially overlaps with a corresponding receptacle of the detachable closure means, particularly when closure means and body are in their final assembly configuration. The groove serving as fluid escape channel preferably extends along the outer surface of the rim portion and/or along the inner surface of the receptacle.

In a further preferred embodiment, the closure means comprises an axially inwardly facing plugging portion and an adjacent flange portion. Here, in an assembly configuration, the flange portion axially abuts against an axial end section or axial end face of the substantially cylindrical body. The plugging portion of the closure means then serves as a plug-like seal extending almost entirely across the circular cross-section of the body.

Also here, at least one fluid escape channel extends in the interface area of body and closure means.

According to a further preferred embodiment, the closure means and the body are releasably joined by means of a form- and/or force-fitting connection. For instance, body and closure means may comprise positive locking means, such as a snap fit or screw threaded connection. Additionally or alternatively, shape and geometry of interface sections of body and closure means may provide a tight fit or they may be frictionally engaged. In this configuration, body and closure means are releasable by applying a withdrawal force above a predefined threshold.

According to another embodiment, the at least one fluid escape channel axially intersects the piston. The piston may be centrally intersected by the fluid escape channel, while its peripheral wall is frictionally engaged with the inner sidewall of the body. Alternatively fluid escape channel may be an axial groove along the length of the piston which breaches the seal between the piston and the inner sidewall of the body. Size and location of the piston-intersecting fluid escape channel is further adapted to the size and configuration of the piston rod or its pressure piece that operably engages with a respective end face of the piston. In this embodiment, the mutual abutment of piston and piston rod is such that the piston rod does not seal the fluid escape channel that intersects the piston.

According to another embodiment, the at least one fluid escape channel intersects the closure means. The only constraint on the location and form of the fluid escape channel is that it must not directly connect the interior of the body to the interior of the cupped receptacle of the closure means.

According to another preferred embodiment, the body comprises radially inwardly extending retention elements at its axial end sections. By means of these retention elements, the piston is prevented from sliding out of the body. Typically, the retention elements are of prong- or tooth-like shape. The retention elements may extend to the free end of the body and may comprise an axially and radially inwardly directed rising edge which allows for an axially inwardly directed insertion of the piston into the interior of the body. Towards the axial center of the body, the retention elements comprise a steep edge that prevents a falling out or withdrawal of the piston from the body.

According to a further independent aspect, the present invention also relates to a drug delivery device and preferably to a pen-type injector allowing a user or patient to select and to administer a dose of a medicinal product by himself, preferably by injection. Said drug delivery device comprises a housing, a drive mechanism and at least one cartridge holder. The drug delivery device is further equipped with a training or test cartridge according to the present invention, having a body, a piston and a closure means.

The cartridge is assembled in the cartridge holder in such a way, that a piston rod or a drive sleeve of the drive mechanism is operably engaged with the piston of the cartridge. Preferably, the drug delivery device is of re-usable type. Hence, the training cartridge can be replaced by a genuine cartridge filled with medicinal product to be administered to the patient on a regular basis.

In a further independent aspect the invention also refers to a method of resetting a cartridge for a drug delivery device, in particular for resetting a training or test cartridge. Said method is applicable to cartridges that comprise a body of substantially cylindrical shape, a piston slidably disposed in the body in an axial direction and a closure means being disposed at a first axial end portion of the body. The cartridge comprises a cupped cavity substantially sealable by means of the axially moveable piston. Hence, body, piston and the closure means confine an interior volume.

The interior volume is further coupled to the exterior via at least one fluid escape channel, which allows for a translational displacement of the piston. Typically, under the effect of a piston rod of a drive mechanism of a respective drug delivery device, the piston becomes subject to a distally directed movement towards the closure means. After the piston reaches a distal stop position in the vicinity of the closure means, that typically corresponds to a last dose stop of the drug delivery device, the method of resetting the cartridge comprises the steps of detaching the closure means from the first end portion of the cylindrical body and arranging the closure means at a second end portion of the body, diametrically opposite to the first end portion. In this way and due to a symmetric design of the body, the entire reset cartridge can be reassembled in the drug delivery device by a simple rotation of 180°, wherein the piston effectively returned to its initial position.

It will be apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

Without limitation, the present invention will be explained in greater detail below in connection with preferred embodiments and with reference to the drawings in which.

DETAILED DESCRIPTION

The cartridge 10 as illustrated in FIGS. 1 through 8 comprises an elongated hollow body 12 of substantially cylindrical shape, a piston 18 slidably disposed in the body 12 along the body's long axis specifying an axial direction. The cartridge 10 further comprises a closure means 14 adapted to seal one axial end portion of the body 12. The body 12 and the closure means 14 constitute a cartridge housing of substantially cupped geometry. The piston 18 typically comprising a circular cross-section is frictionally engaged with the inner surface of the body 12. The interior volume 16 confined by the body 12, the closure means 14 and the piston 18 is coupled to the exterior via at least one fluid escape channel 28 extending in an interface section of body 12 and closure means 14.

Figure 1:
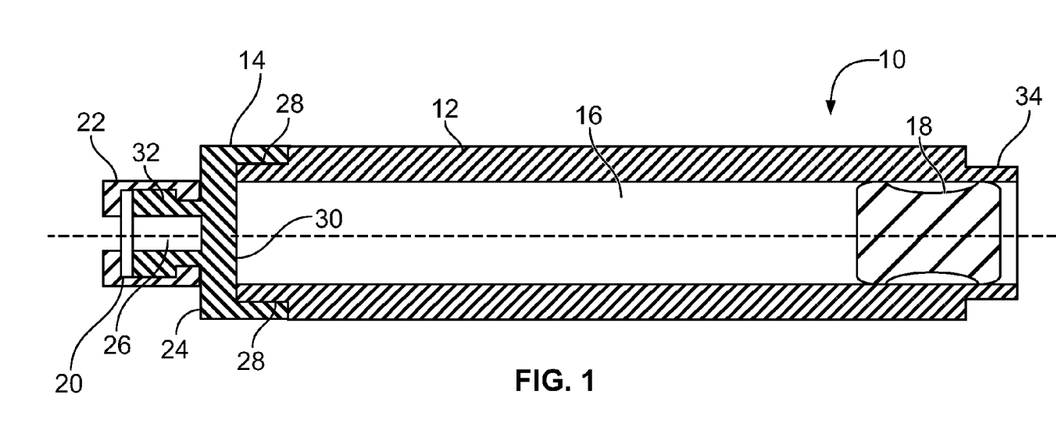
FIG. 1 schematically illustrates a first embodiment of a training cartridge comprising a detachable closure means.
Figure 2:
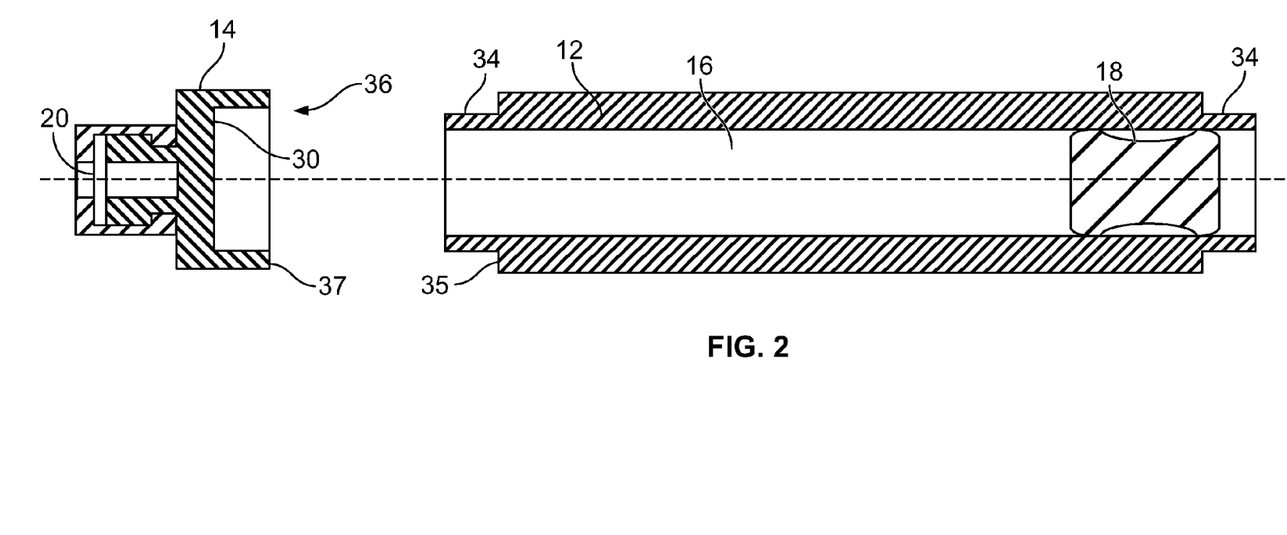
FIG. 2 shows the cartridge with disassembled closure means.
Figure 3:
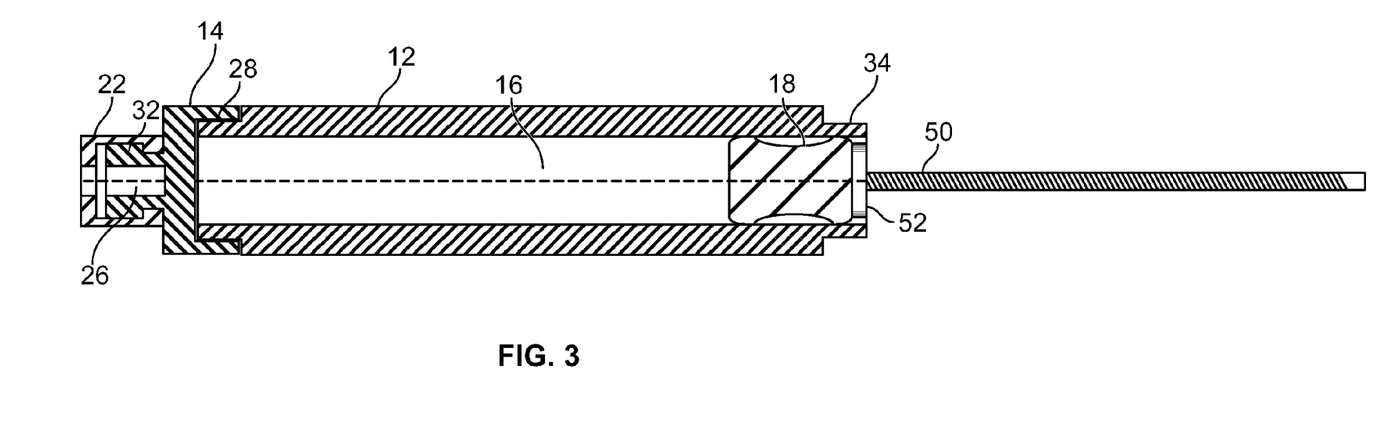
FIG. 3 shows the cartridge according to FIG. 1 operably engaged with a piston rod of a drug delivery device.

The closure means 14 comprises an axially inwardly directed end wall 30 that abuts with an axial end of the body's 12 cylindrical wall. In the embodiment according to FIGS. 1 to 8, the body 12 comprises a stepped down rim portion 34 at both of its axial end sections. In an assembly configuration, as illustrated in FIG. 1, the rim 34 radially overlaps with the sidewall of a corresponding receptacle 36 of the closure means 14. In order to provide at least one fluid escape channel 28 in the intersection of closure means 14 and body 12, respective contact surfaces of rim 34, receptacle 36 and their corresponding socket 35 and/or substantially radially extending end face 37 comprise at least one groove, that serves as fluid escape channel and which allows for an escapement of a fluid or a gaseous medium when the piston 18 is subject to a distally directed axial movement, that is, a movement towards the closure means 14.

For the formation of at least one fluid escape channel, it may already be sufficient to provide a radially extending groove at the axial end face of the rim 34 of the body 12 and wherein this radial groove extends into an axially extending groove at the circumference of the rim 34 and is finally coupled to another radially extending groove in the socket portion 35 of the body 12.

In a similar way, respective grooves can be provided in the end wall 30, the sidewall of the receptacle 36 and the end face 37 of the closure means 14.

The closure means 14 further serves as a means for hermetically dividing the interior volume 16 and a receptacle 26 formed at the outside portion of the closure means 14. The receptacle 26 is sealed by a septum 20, that is commonly designed as rubber stopper providing an air-tight seal but being pierceable by piercing elements such as needles or cannulae. The septum 20 may be fixed to the axially extending socket portion 32 by means of a fastening element 22, e.g. by means of a clamping element, such as an aluminium crimp.

The septum 20 is adapted to be pierced by a not further illustrated piercing element, such as an infusion needle, a cannula or the like. Due to the hermetic separation from the inner volume 16, a supply of a fluid to the piercing element is effectively prevented. In this way, any cross contamination of a training cartridge 10 and its inner volume can be effectively inhibited. Also, the user can simulate the device handling under realistic conditions without actually injecting a dose of water or placebo.

The closure means 14 comprises a radially extending shoulder 24 that substantially matches the radial circumference of the body 12. The socket portion 32 and/or the shoulder 24 are adapted to but against a respective receptacle of a not further illustrated cartridge holder of a drug delivery device in order to secure and to fasten the cartridge 10 inside the drug delivery device.

The outer dimensions of the training cartridge 10 are substantially equal to those of a genuine cartridge filled with a medicinal product. Typically, the training cartridge 10, in particular its body 12 and/or its closure means 14 are manufactured from a transparent material, which allows a user to visually follow the position and movement of the piston 18. Compared to a genuine cartridge, the present training cartridge 10 does not have to be filled with water or with a placebo. Preferably, the interior volume 16 is filled with ambient air, which is expelled from the interior volume 16 by way of the at least one fluid escape channel 28 as the piston 18 is driven towards the closure means 14. Once the ambient air has exited by way of the fluid escape channel 28 it is then free to escape from the drug delivery device by a number of means, e.g. through the device mechanism, through the connection between the device and the cartridge holder etc.

Compared to a genuine product-filled cartridge, the friction of piston 18 and inner sidewall of the body 12 can be at least slightly increased Also, or alternatively, the at least one fluid escape channel 28 may be appropriately sized such that it creates a recognizable damping effect on the advance of the piston 18 by restricting the exit flow of the ambient air initially contained in the interior volume 16.

Either the increase of friction of piston 18 and inner sidewall of the body 12 or the damping effect of the at least one fluid escape channel 28 or a combination of both may be applied in order to create mechanical resistance against the advance of the piston 18, which in a genuine injection of medicament would be provided by the pressure of the liquid drug being expelled from the cartridge via an infusion needle or the like. In this way the training cartridge can provide a realistic and comparable mechanical force feedback when assembled in a corresponding drug delivery device.

The sequence of FIGS. 3 through 8 illustrates the various steps and configurations of the training cartridge 10 in use. In a first step, the training cartridge 10 is assembled and inserted into a preferably re-usable injection device, such as a pen-type injector. A piston 50 with its pressure piece 52 is for instance subject to a priming procedure, during which the pressure piece 52 is brought into contact with the end face of the piston 18. This priming procedure is also required with genuine medicament cartridges and therefore completing the priming process with the training cartridge may form a part of the training process. Now, the drug delivery device can be used for training of the injection step, wherein the piston 18 advances in distal direction towards the closure means 14, typically under the effect of thrust exerted by the piston rod 50.

Figure 4:
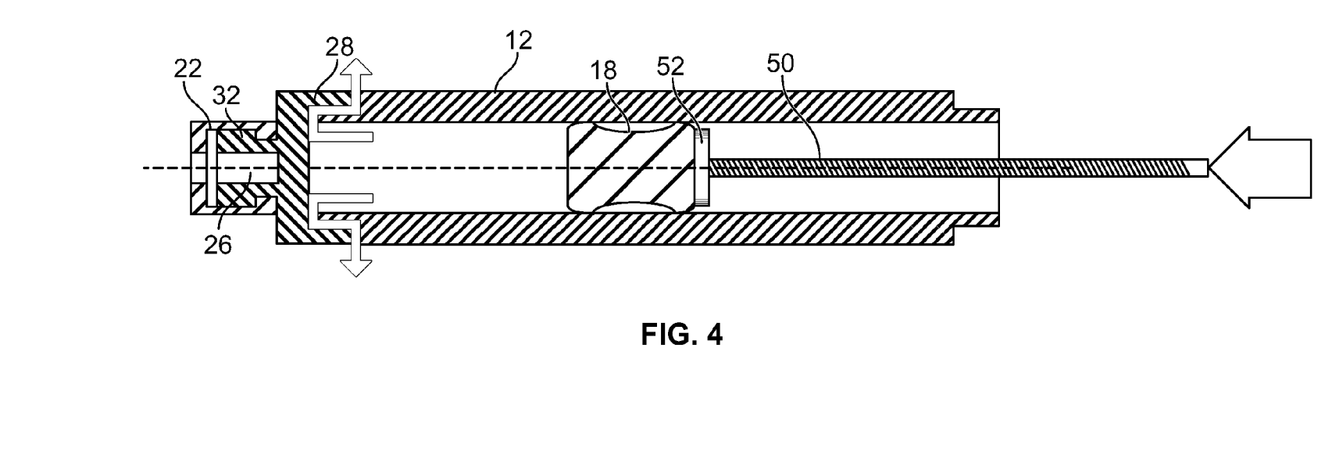
FIG. 4 illustrates the longitudinal displacement of the cartridge's piston.
Figure 5:
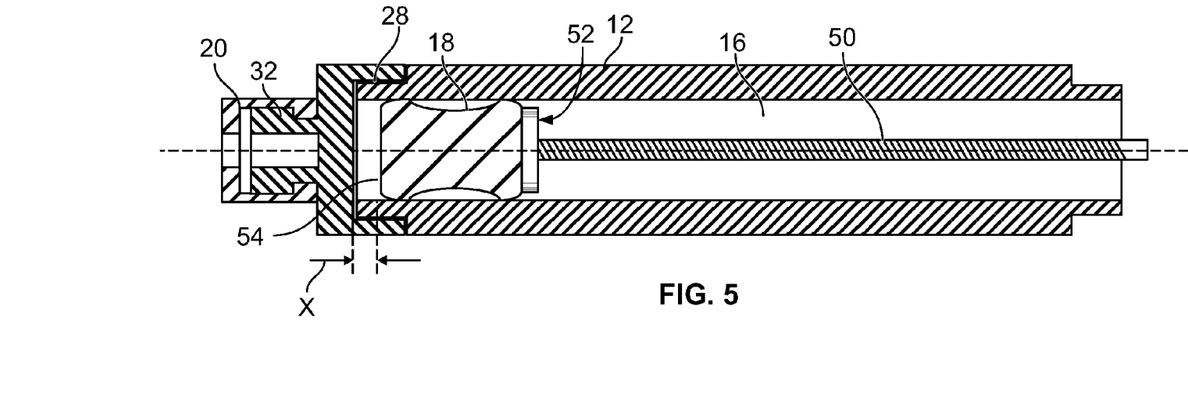
FIG. 5 shows a configuration of the cartridge upon reaching a last dose stop.

By means of the illustrated fluid escape channels 28, the gaseous or liquid medium contained in the interior volume 16 is free to escape in radial direction as illustrated by the radially outwardly pointing arrows in FIG. 4. As soon as a final position of the piston 18 has been reached, as illustrated in FIG. 5, the distal end face 54 of the piston 18 and the end wall 30 of the closure means 14 are separated by a distance X as illustrated in FIG. 5.

Figure 6:
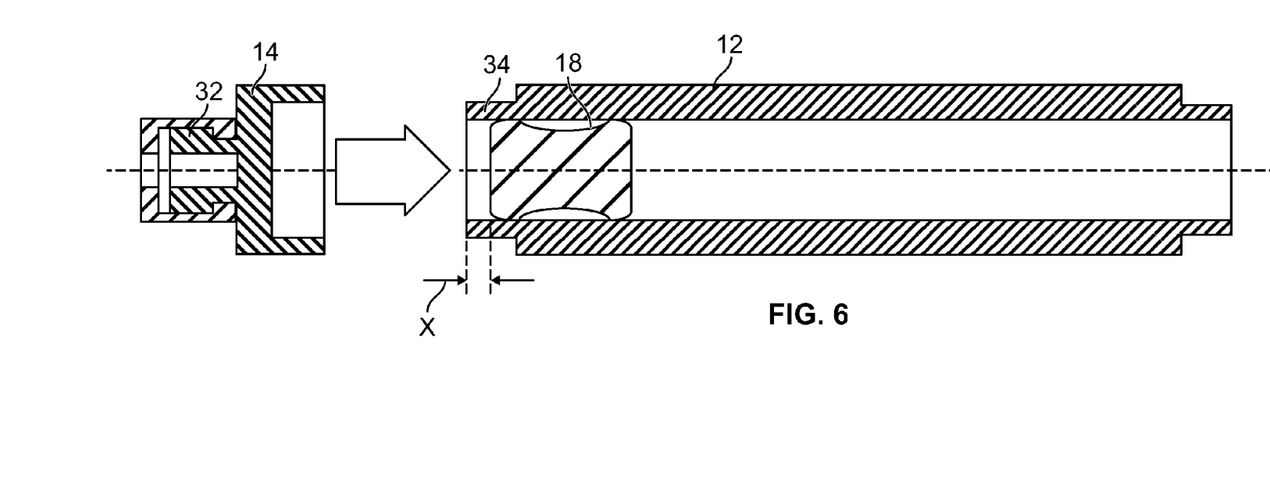
FIG. 6 is illustrative of detaching body and closure means.
Figure 7:
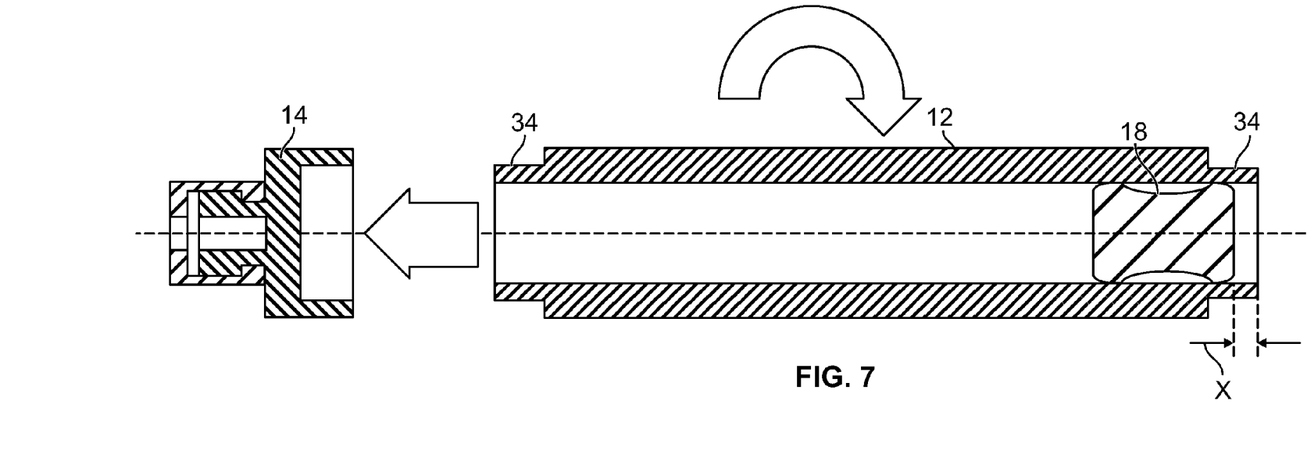
FIG. 7 is illustrative of re-assembling the closure means to an opposite end portion of the rotated body and FIG. 8 shows the reset and reassembled training cartridge.
Figure 8:
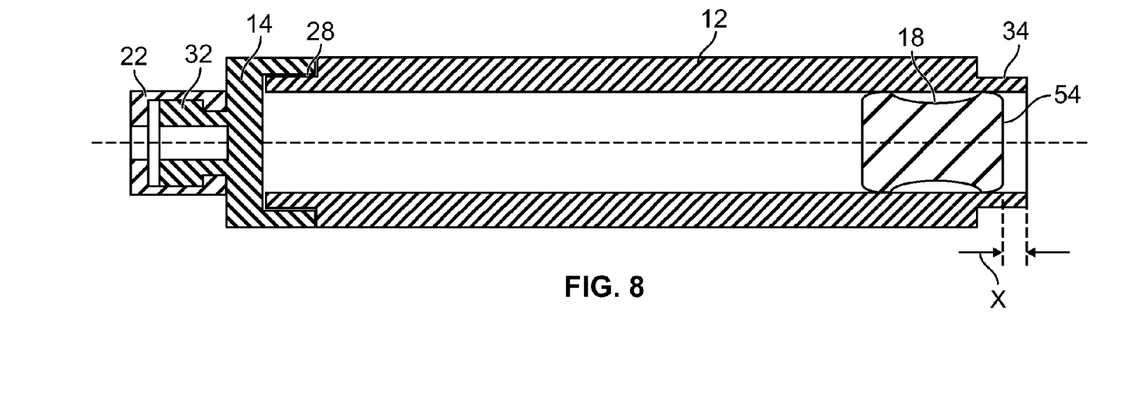

Now, as shown in FIG. 6, closure means 14 and body 12 are disassembled and, as illustrated in FIG. 7, the body 12 becomes subject to a turn over by 180° before the opposite end of the body 12 is reassembled with the closure means 14 as shown in FIG. 8. Since the piston 18 is frictionally engaged with the body 12, its position relative to the body 12 remains substantially unchanged. Consequently, the end face 54 of the piston 18 now points in proximal direction and operably engages with the pressure piece 52 of the drive mechanism of the drug delivery device in a subsequent training procedure.

The disassembling and reassembling of a plug-like closure means 14 to both axial end sections of a cartridge body 12 allows for an easy and elegant resetting and reusing of a training cartridge 10. The length of the body 12 is designed such, that the distance X corresponds to the nominal manufacturing insertion distance of the piston in a genuine cartridge.

Figure 9:
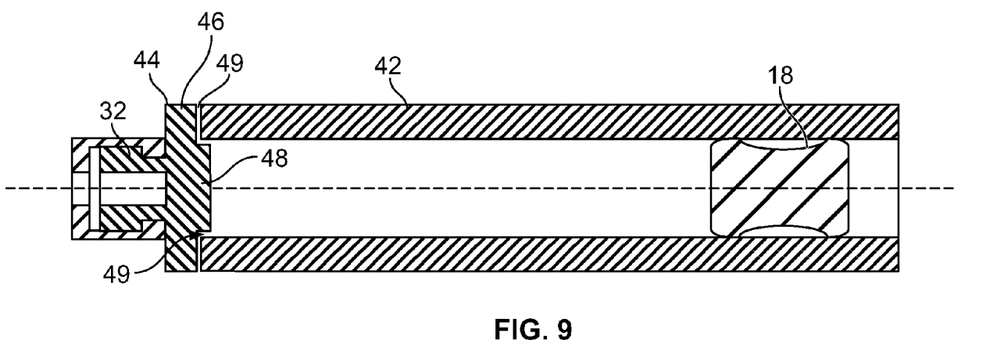
FIG. 9 is illustrative of a second embodiment of a training cartridge in an initial configuration and FIG. 10 illustrates the cartridge according to FIG. 9 in a last dose stop configuration.
Figure 10:
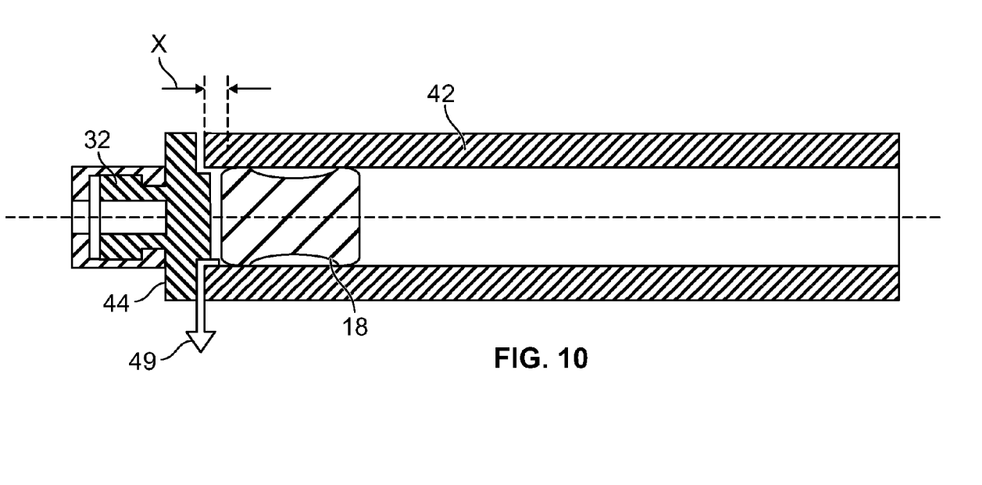

In the embodiment as illustrated in FIGS. 9 and 10, the body 42 is of hollow cylindrical shape. Here, the closure means 44 is designed as plug-like seal, adapted to substantially seal one open end of the body 42. Assembly of closure means 44 and body 42 forms a cupped hollow cavity, which is sealed by means of the frictionally engaged piston 18.

A fluid escape channel 49 is formed in the interface region of closure means 44 and body 42. The closure means 44 comprises a radially extending flange portion 46, which axially abuts with an axial end face of the body 42. Furthermore, the closure means 44 comprises a centrally arranged plugging portion 48, that substantially extends across the entire inner cross-section of the body 42. Also here, the fluid escape channel 49 can be formed by means of radially and/or axially extending adjacently and mutually merging grooves extending in respective contact surfaces of the body 42 and/or of the closure means 44. By means of the at least one fluid escape channel 49, a venting and fluting of the interior volume formed by the body 42, the piston 18 and the closure means 44 can be effectively achieved.

Figure 11:
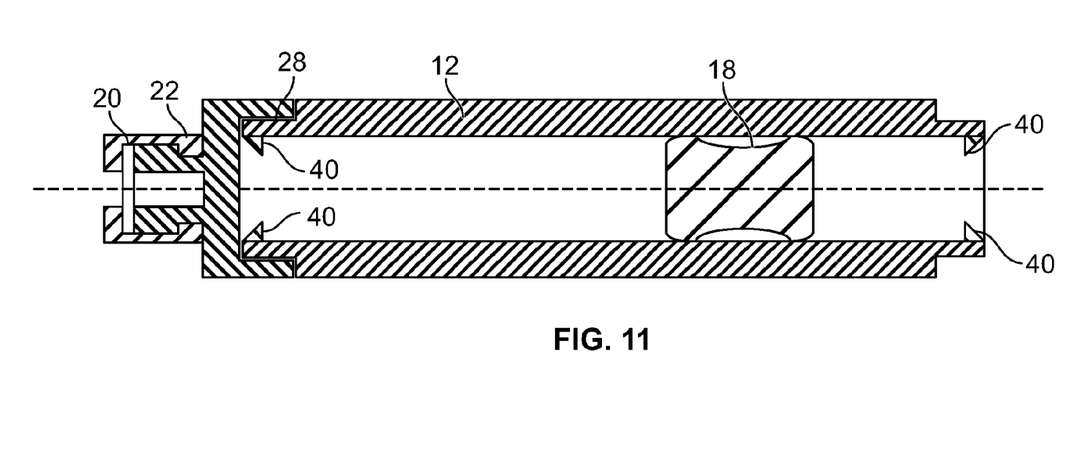
FIG. 11 is illustrative of an embodiment, wherein the body comprises radially inwardly extending retention elements

In the further embodiment according to FIG. 11, the body 12 at its distal end sections further comprises prong-like or tooth-like radially inwardly protruding retention elements 40. Starting from the free end of the rim portion of the body 12, the retention elements 40 comprise a radially and axially inwardly directed slope, allowing for an initial insertion of the piston 18. The axially inwardly directed falling edge of the retention elements 40 in turn prevents unintentional withdrawal of the piston 18 from the body 12.

Figure 12:
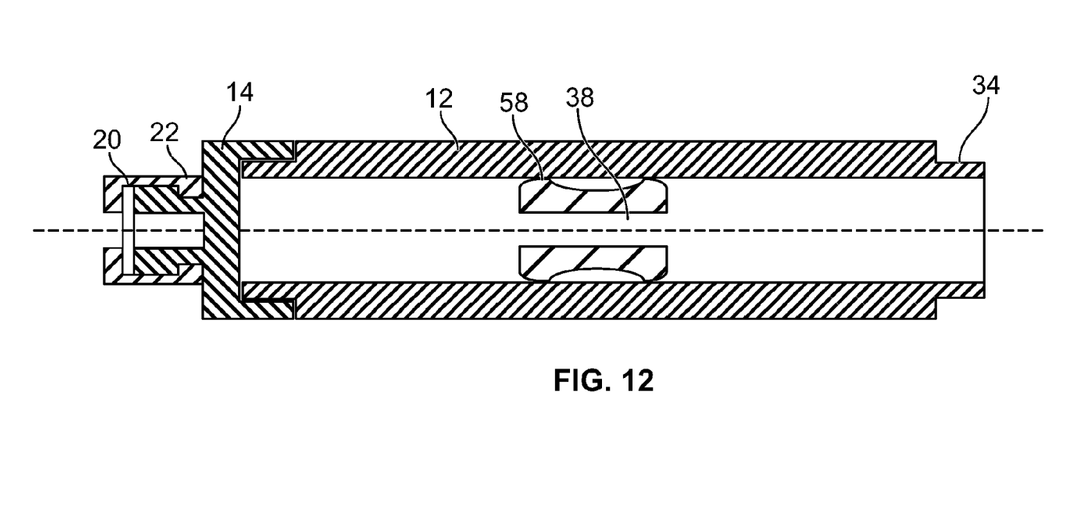
FIG. 12 shows an embodiment with a piston intersected by a fluid escape channel.

In the further embodiment according to FIG. 12, a piston 58 is illustrated, which is axially intersected by a fluid escape channel 38. Here, the gaseous or liquid media contained in the interior volume 16 may escape through the central bore 38 of the piston 58, while the piston 58 itself remains frictionally engaged with the body 12 for providing a realistic force feedback to the user during a training sequence. In this embodiment, it is beneficial when the mutual abutment of a piston's 58 end face with a pressure piece 52 or a piston rod 50 allows and supports the intended escapement of a fluid.

The invention claimed is:

1. A training cartridge for a drug delivery device comprising:
   a body of substantially cylindrical shape and extending along an axial direction,
   a piston slidably disposed in the body in the axial direction,
   a closure means disposed at an axial end portion of the body and sealing the end portion of the body, wherein the closure means comprises an axially inwardly facing end wall that abuts with an axial end face of the body or wherein the closure means comprises a radially outwardly extending flange portion which axially abut with the axial end face of the body,
   wherein the body, the piston and the closure means confine an interior volume permanently coupled to an exterior via at least one fluid escape channel,
   wherein the at least one fluid escape channel comprises a groove in a contact surface of an interface section of body and closure means, and
   wherein the fluid escape channel forms a permanent passage for a liquid or a gas contained in the interior volume while the end wall or the flange portion of the closure means is in abutment with the axial end face of the body.

2. The training cartridge according to claim 1, wherein the closure means comprises an inward facing fluid-impenetrable end wall and an outward facing socket portion.

3. The training cartridge according to claim 2, wherein the socket portion comprises a septum sealing a cupped receptacle being separated from the interior volume.

4. The training cartridge according to claim 1, wherein the closure means is releasably connectable with both axial end portions of the body.

5. The training cartridge according to claim 4, wherein the body at its axial end portion comprises a stepped down rim portion radially overlapping with a corresponding receptacle of the closure means.

6. The training cartridge according to claim 1, wherein the fluid escape channel is non-sealable.

7. The training cartridge according to claim 1, wherein the fluid escape channel at least partially extends in an interface section of body and closure means in radial direction.

8. The training cartridge according to claim 1, wherein the closure means is integrally formed with the body.

9. The training cartridge according to claim 1, wherein the closure means comprises an axially inwardly facing plugging portion and an adjacent flange portion, wherein in an assembly configuration, the flange portion axially abuts against an axial end section of the body.

10. The training cartridge according to claim 1, wherein the body and the closure means are releasably joined by means of a force- and/or form-fitting connection.

11. The training cartridge according to claim 1, wherein the body comprises radially inwardly extending retention elements at its axial end sections adapted to prevent the piston from sliding out of the body.

* * * * *